United States Patent
Aluisi

(10) Patent No.: US 6,213,360 B1
(45) Date of Patent: Apr. 10, 2001

(54) SYSTEM AND METHOD FOR CHANGING A GLOVE ATTACHED TO A GLOVE BOX

(75) Inventor: Alan Aluisi, Aruada, CO (US)

(73) Assignee: The United States of America as represented by the United States Department of Energy, Washington, DC (US)

( * ) Notice: Subject to any disclaimer, the term of this patent is extended or adjusted under 35 U.S.C. 154(b) by 0 days.

(21) Appl. No.: 09/657,004

(22) Filed: Sep. 7, 2000

(51) Int. Cl.⁷ .................................................. A47G 25/80
(52) U.S. Cl. ................................................................ 223/111
(58) Field of Search ................................ 223/111, 78, 79, 223/80

(56) References Cited

U.S. PATENT DOCUMENTS

| | | | |
|---|---|---|---|
| 4,123,123 | * 10/1978 | Sato et al. ............................... | 312/1 |
| 4,915,272 | * 4/1990 | Vlock ..................................... | 223/111 |
| 5,058,785 | * 10/1991 | Rich et al. ............................. | 223/111 |
| 6,021,935 | * 2/2000 | Yonezawa ............................. | 223/111 |

* cited by examiner

*Primary Examiner*—Bibhu Mohanty
(74) *Attorney, Agent, or Firm*—Connie Berg; Mark P. Dvorscak; Paul A. Gottlieb

(57) ABSTRACT

A system for changing the gloves of a glove box. The system requires the use of a new glove and a glove change ring to form a temporary secondary barrier to the exchange of atmospheres between the inner glove box and the room in which the glove box is operated. The system describes specific means for disengaging a used glove from the glove box port. The means for disengaging the used glove include use of a glove change hook and use of a glove with an attached tab for use in removal. A method for changing the gloves of a glove box is also described.

12 Claims, 3 Drawing Sheets

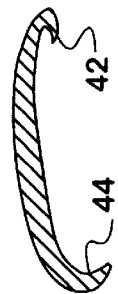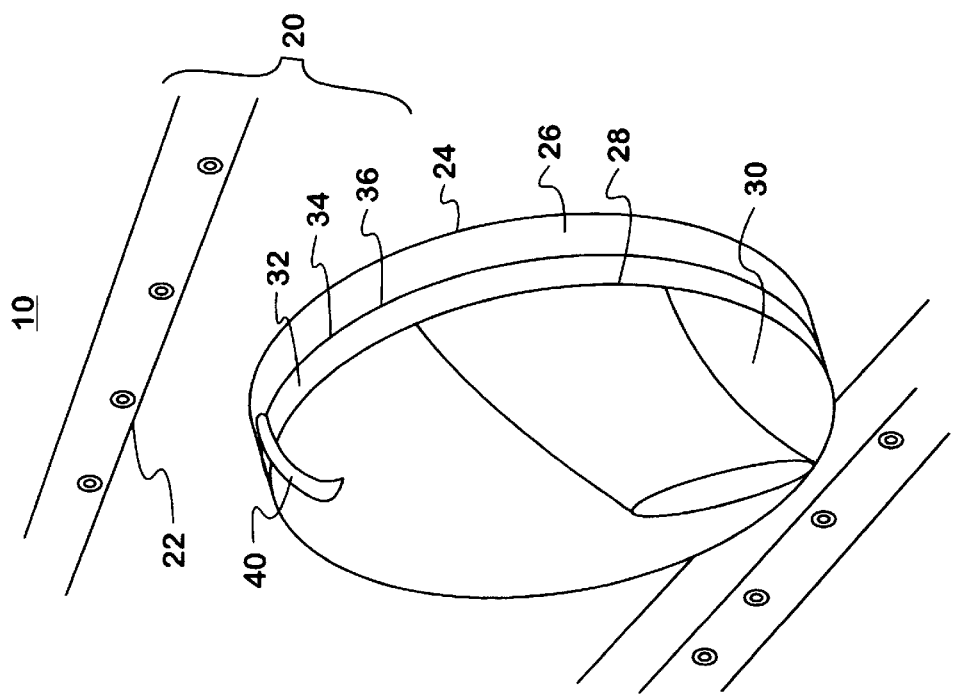

SYSTEM AND METHOD FOR CHANGING A GLOVE ATTACHED TO A GLOVE BOX

U.S. GOVERNMENT RIGHTS

The United States Government has rights in this invention pursuant to Contract No. DE-AC34-95RF00825 between the U.S. Department of Energy and Kaiser-Hill Company.

BACKGROUND OF THE INVENTION

This system and method are an improvement in the art of changing the glove of a glove box. A glove box is a sealed enclosure for handling radioactive, chemical, hazardous, or biohazardous material. An operator may manipulate objects inside the glove box by inserting a hand into a rubber glove that is sealed at an entrance port to the glove box.

Periodically, the gloves attached to the port must be changed. When changing the glove on a glove box port, great care must be taken to avoid box breaching. Box breaching occurs when the glove box atmosphere is allowed to escape into the room in which the box is being used. Escape of the glove box atmosphere may occur even when there is an attempt to maintain negative pressure within the box and will expose the operator and anyone near by to the hazards associated with contents of the box.

Glove changes can be accomplished by completely shutting down glove box operations and evacuating the glove box of all materials and gases. The operator may then remove the used glove and then attach a replacement glove at the operator's leisure as long as the change is complete before the glove box is put back in service.

Glove changes may be accomplished if the glove box is in service. However, this glove change method requires the operator to pull the old, used glove from the from the entrance port with one hand, while securing the new, replacement glove over the port with the other hand. The operator is often required to struggle to "muscle" the old, used glove from the port for several minutes; and during this process, the operator may briefly and unintentionally allow the new glove to come away from the port, exposing the room air to the box atmosphere. This unintentional exposure of the box atmosphere to the room is a common occurrence during difficult glove changes.

The glove changing system and method described here requires the use of at least two gloves and incorporates a primary seal (between the old, used glove and the entrance port) and a secondary seal (between the new, replacement glove and the entrance port). This system and method also incorporate the use of a disengaging means to assist in the removal of the old, used glove from the entrance port. The system and method facilitate safer, easier glove box glove changes.

Some methods for fixing a glove to a glove box have described a dual glove procedure for glove changes (see U.S. Pat. No. 4,123,123 ("'123")). The '123 patent describes a method using gloves that have an extended fin portion (i.e., longer end opposite the fingers of the glove) that folds over the port. During glove replacement, a new glove is placed on the exterior side of the old glove and a hole closing bung is inserted within the new glove to maintain a seal at the port as the old glove extended fin is released from the port. The new glove extended fin is then attached to the port and the operator completely removes the old glove by "jerking" it into the glove box.

The present system and method are an improvement over the '123 patent because the area of overlap between the old and new gloves is much smaller than the overlap of the '123 patent. No jerking action is required to remove the old glove, rather this system and method provide a mechanism to grasp and gently peel the old glove from the port of the glove box.

OBJECTS OF THE INVENTION

The object of this system is to facilitate safer and easier glove box glove changes than is currently possible using existing processes and tools. The system incorporates the use of at least two gloves to form primary and secondary seals on the glove box with the use of a disengaging means to assist with the removal of the old, used glove from the glove box port.

Another object of the invention is to provide specific means for removing an old, used glove from the glove box port. Two specific means for achieving the removal of the used glove include the use of a glove change hook and the use of a tabbed glove.

A further object of this invention is to provide a method for changing the glove of a glove box while avoiding box breaching.

SUMMARY OF THE INVENTION

A system for changing the gloves of a glove box. The system requires the use of a new glove and a glove change ring to form a temporary secondary barrier to the exchange of atmospheres between the inner glove box and the room in which the glove box is operated. The system describes specific means for disengaging a used glove from the glove box port. The means for disengaging the used glove include the use of a glove change hook or use of a glove with an attached tab for use in removal. A method for changing the gloves of a glove box is also described.

BRIEF DESCRIPTION OF THE DRAWINGS

FIG. 1 depicts the glove changing system in use with the glove change hook.

FIG. 1a is a standard glove change hook.

FIG. 1b is a concave glove change hook.

FIG. 1c is a curved gloved change hook.

FIG. 1d is a glove change hook with a ring-shaped handle.

DETAILED DESCRIPTION OF THE PREFERRED EMBODIMENT

Figure 2A:
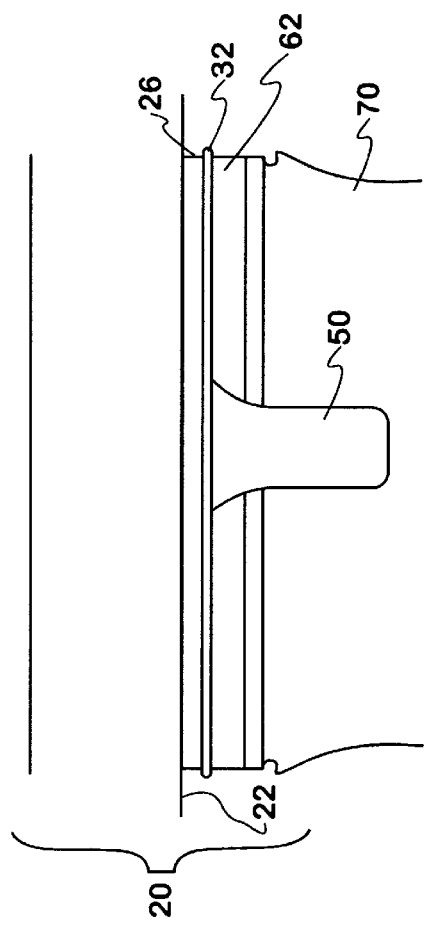
FIG. 2a is a detail of the tabbed glove on a glove box.
Figure 2:
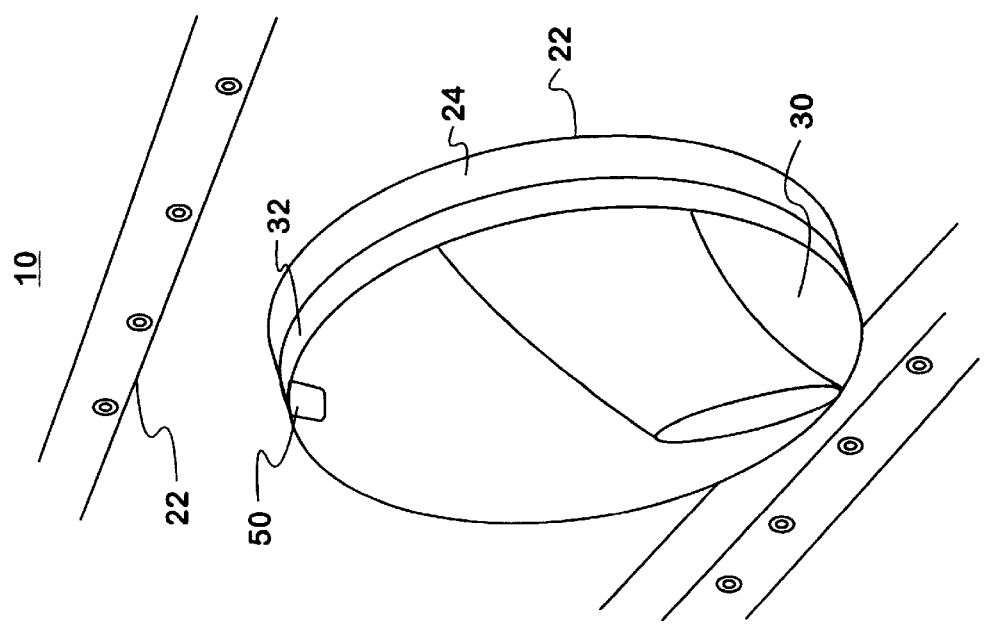
FIG. 2 depicts the glove changing system in use with the tabbed glove.
Figure 3:
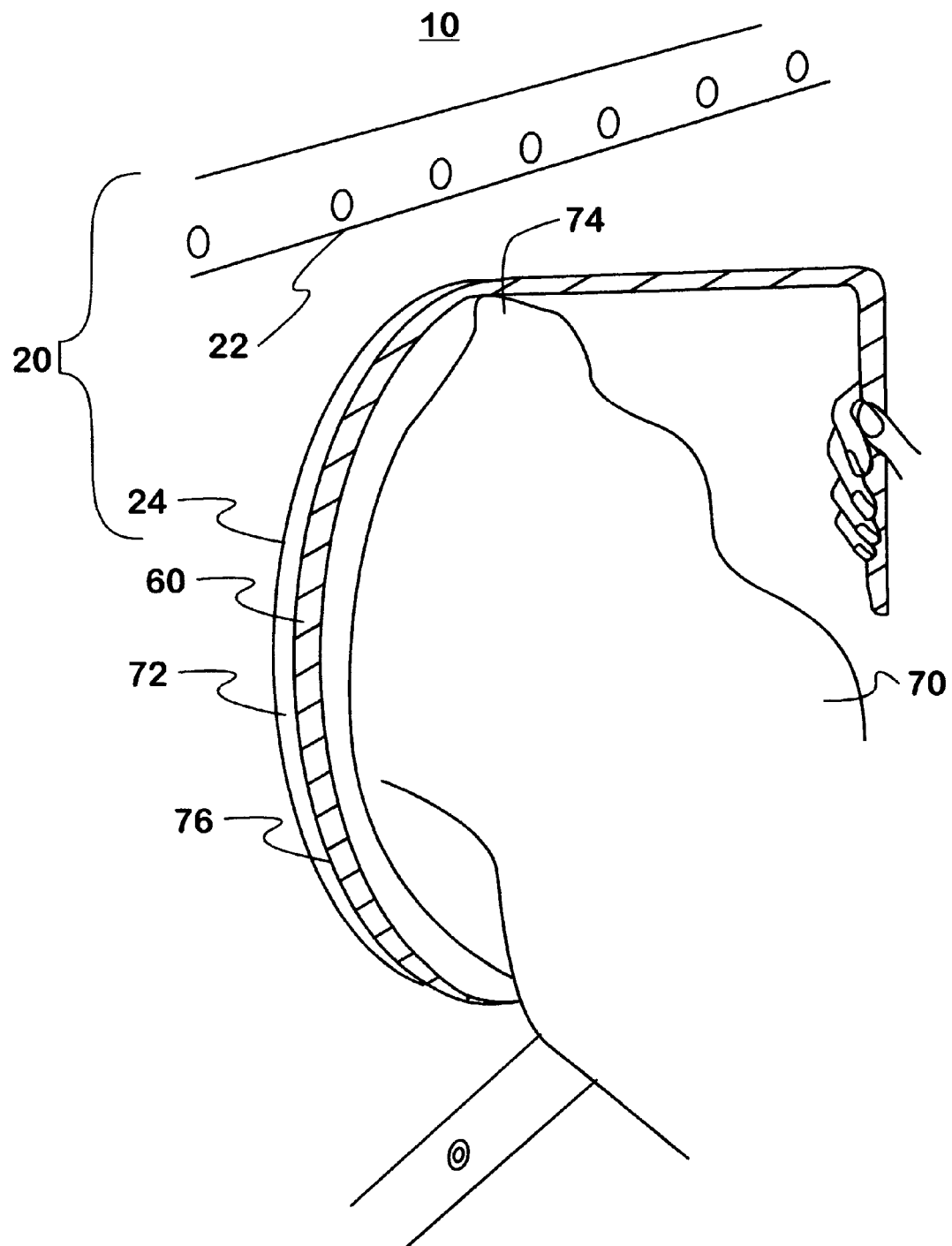
FIG. 3 depicts the glove changing, system in use with the new glove and glove change ring.

FIGS. 1 and 2 depict the glove changing system 10 with the old glove 30 in place prior to the formation of the secondary seal by the new glove 70 and the glove change ring 60 (both shown in FIG. 3). The old glove 30 has a cuff 32 at its open end 36. Similarly, the new glove 70 has a cuff 72 (shown in FIG. 3) at its open end 76 (shown in FIG. 3). The cuffs 32 and 72 have elastic properties that allow the cuffs 32 and 72 of the gloves 30 and 70 to be stretched (expanded) to dimensions larger than the shoulder 26 of the entrance port 24 to the glove box 20 and then the cuffs 32 and 72 will contract toward their original size and shape forming a seal between the interior of the glove box 20 and the atmosphere in the room in which the glove box 20 is being used. The shoulder 26 is at least long enough (as measured from the outer wall of the glove box 20) to accommodate the old glove 30 cuff 32 and the new glove 70 cuff 72. The cuffs are approximately equal in width.

The system 10 for changing the gloves requires that the old glove 30 that has been used in the interior of the glove box 20 be worked toward the edge of the shoulder 26 prior to the formation of the secondary seal using the new glove 70 that is attached to the glove change ring 60. Once the old glove 30 has been worked toward the end of the shoulder 26, the new glove 70 is secured to the shoulder 26 between the old glove 30 and the outer wall 22 of the glove box 20. During the time that the new glove 70 and old glove 30 are both attached to the shoulder 26 the interior atmosphere of the glove box 20 is separated from the room atmosphere by two seals. The primary seal is formed by the attachment of the old glove 30 to the shoulder 26 of the entrance port 24. The secondary seal is formed by the attachment of the new glove 70 to the shoulder 26 of the entrance port 24 so that the secondary sealed is formed completely between the old glove 30 and the outer wall 22 of the glove box 20.

Once the secondary seal has been formed by the new glove 70, the operator may reach into the new glove 70 and break the primary seal of the old glove 30 with a means for disengaging the old glove 30. The disengaging means allows the operator to loosen and gently remove the old glove 30 from the shoulder 26. The operator may then place the old glove 30 completely within the interior of the glove box 20 so that the old glove 30 may be properly discarded.

The disengagement means depicted in FIGS. 1, 1*a*, 1*b*, 1*c*, and 1*d* are glove change hooks 40. The glove change hook is an elongated tool that has a tight curve 42 designed to partially encircle the bead 34 on the old glove 30. The glove change hook 40 may be used to partially encircle the open end of the old glove 30 and aid in its disengagement even if the old glove 30 does not have a bead 34 formed at or near the open end of the glove 30.

The glove change hook 40 is intended to be disposable. The hook 40 must be rigid enough to maintain its strength and shape during use and, therefore, may be manufactured from steel or other rigid metal or alloy, or may be molded or extruded using a rigid plastic polymer. The shape of the glove change hook 40 may vary as shown in FIGS. 1*a*–1*d*.

FIG. 1 a depicts a glove change hook 40 that maintains a generally linear shape between the tightly curved 42 end and the handle 44. FIG. 1*b* shows a glove change hook 40 that maintains a concave curve between the tightly curved 42 end and the handle 44. FIG. 1*c* shows a glove change hook 40 with a slight serpentine curve between the tightly curved 42 end and the handle. FIG. 1*d* shows a glove change hook 40 with a ring-shaped handle 44. The glove change hook 40 will be effective if the width and depth are equal or nearly equal (as with a wire). The width is the dimension that would parallel to the floor (not shown) as the hook 40 is oriented in FIG. 1. Preferably the width of the hook 40 is greater than its depth for added leverage when disengaging the old glove 30 from the shoulder 26 of the port 24.

The disengagement means depicted in FIGS. 2 and 2*a* is a tab 50 attached at or near the open end of the old glove 30. The tab 50 is added during the glove manufacturing process and is not offered as an accessory or after market product. The operator to loosen and gently remove the old glove 30 from the shoulder 26. The operator may reach into the new glove 70 and grasp the tab and pull radially and outwardly to break the primary seal formed between the old glove 30 and the shoulder 26. The operator may then place the old glove 30 completely within the interior of the glove box 20 so that the old glove 30 may be properly discarded. FIG. 2*a* is a detailed depiction of a tabbed 50 new glove 70 sealed to the shoulder 26 of the entrance port 24 to the glove box 20.

FIG. 3 shows the system after the secondary seal has been formed between the new glove 70 and the shoulder 26. A slight bulge 74 forms briefly as the disengagement means is used to initiate the break of the primary seal formed between the old glove 30 and the shoulder 26.

To remove the old glove 30 and replace it with a new glove 70. The glove port band 62 must first be removed from around the old glove 30. The band 60 secures the old glove 30 to the shoulder 26 of the port 24 until the glove changing method or system 10 for changing the gloves is initiated. The old glove 30 is worked toward an edge 28 of the shoulder 26 to loosen the glove 30 for subsequent removal and to prevent tearing of the old glove 30 that may require the operator to remove the old glove 30 in a piecemeal fashion.

The new glove 70 is attached by its open end 76 to the glove change ring 60. The operator places a hand in the new glove 70 and grasps the disengaging means, and secures the hook 40 under the bead 34 of the old glove 30. The disengaging means may be a glove change hook 40 or a tab 50 attached to a glove. The open end 76 of the new glove 70 is folded to double over the outside of the glove 70 toward the fingers of the glove 70. The open end 76 of the new glove 70 is placed on the shoulder 26 of the glove box 20 port 24 between the old glove 30 and the outer wall 22 of the glove box 20. The new glove 70 will completely surround the old glove 30 and form a secondary seal to prevent the migration of the interior glove box atmosphere to the room.

The old glove 30 is then removed by pulling the disengagement means in a slight radial direction from the port 24 and outwardly from the glove box 20 Constant pressure should be kept against the glove change ring 60 during the removal of the old glove 30 to reduce the possibility that the secondary seal created between the new glove 70 and the shoulder 26 will be broken. The old glove 30 is then pushed entirely into the glove box 20 and will be properly disposed of. The glove port band 62 is tightened over the cuff 72 of the new glove 70. The new glove 70 is then ready for use.

Alternatively, the new glove 70 may be positioned on the shoulder 26 between the old glove 30 and the outer wall 22 of the glove box 20, or pressed against the outer wall 22 of the glove box 20 prior to the operator grasping the tab 50 or securing the hook 40 under the old glove 30. The operator will then blindly feel for the disengagement means and then grasp the tab 50 or secure the hook 40 and pull for removal of the old glove 30.

What is claimed is:

1. A glove changing system for use with a sealed glove box, comprising:

an old glove having an old glove open end, where said old glove open end has an attachment cuff that is capable of expanding and contracting and forms a seal on a shoulder of an entrance port to an interior side of said glove box, said shoulder having a length at least two times said attachment cuff as measured from an outer wall of said glove box;

a replacement glove having a replacement glove open end, where said replacement glove open end has an attachment cuff capable of expanding and contracting and is attached to a glove change ring, said glove change ring and the replacement glove are attached to said shoulder between said old glove and said outer wall of said glove box to form a secondary seal; and a means for disengaging said old glove from said port such that said secondary seal provided by said replacement glove remains intact.

2. A glove changing system according to claim 1, wherein said old glove open end and said replacement glove open end are encircled by a continuous bead.

3. A glove changing system according to claim 2, wherein said disengagement means is a glove change hook, comprising:

an elongated device having a first end and a second end where said first end comprising a tight curve dimensioned to partially encircle said bead of said old glove where said old glove open end contacts said shoulder of said port and where said second end is a handle.

4. The glove changing system according to claim 3, wherein said handle and said tight curve in combination from a continuous concave surface.

5. The glove changing system according to claim 3, wherein said handle of said glove change hook has a ring shape.

6. The glove changing system of 3, wherein said glove change hook is made of a material selected from a group consisting of: steel, other rigid metal, and rigid plastic.

7. The glove changing system of claim 3, wherein said glove change hook has both a width and depth where said width exceeds said depth.

8. A glove changing system according to claim 1, wherein said disengagement means is a tab attached to said old glove.

9. A method for changing a glove attached to a glove box, comprising the steps of:

removing a glove port band that tightens an attachment cuff of an old glove to a shoulder of a port of said glove box;

working said old glove toward an edge of said shoulder of said port while maintaining a seal so as to prevent a glove box atmosphere from escaping said glove box;

attaching an open end of a new glove circumferentially to glove change ring;

donning said new glove while said new glove is attached to said glove change ring where said new glove encircles the hand of an operator;

grasping a means for disengaging said old glove from said port;

folding said open end of said new glove that is attached to said glove change ring toward the fingers of said new glove and positioning said open end of said new glove against an outer wall of said glove box such that said new glove completely surrounds said old glove and said port to create a secondary seal to prevent a glove box atmosphere from mixing with a room atmosphere during the glove change procedure;

removing said old glove by pulling a means for disengaging said old glove radially and outwardly from said port;

pushing said old glove completely into said glove box;

separating said glove change ring from said new glove; and tightening said new glove over said shoulder and around said port with said glove port band.

10. The method for changing a glove attached to a glove box according to claim 9, wherein the step of grasping the means for disengaging said old glove from said port further comprises the steps of:

sliding a hook having a profile designed to fit a bead on said glove under said bead before folding said open end of said new glove that is attached to said glove change ring toward the fingers of said new glove and positioning said open end of said new glove against an outer wall of said glove box; and lifting the bead of the old glove from a point of attachment on said shoulder.

11. The method for changing a glove attached to a glove box according to claim 10, wherein the step of folding said open end of said new glove that is attached to said glove change ring toward the fingers of said new glove is accomplished before sliding said hook under said bead.

12. The method for changing a glove attached to a glove box according to claim 9, wherein the step of grasping a means for disengaging said old glove from said port further comprises the step of grasping a tab attached to said old glove at a point of attachment of said old glove to said shoulder of said port.

* * * * *